(12) United States Patent
Akiba et al.

(10) Patent No.: US 9,545,201 B2
(45) Date of Patent: Jan. 17, 2017

(54) FUNDUS OBSERVATION APPARATUS

(75) Inventors: Masahiro Akiba, Tokyo (JP); Atsushi Kubota, Tokyo (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 20 days.

(21) Appl. No.: 13/608,444

(22) Filed: Sep. 10, 2012

(65) Prior Publication Data
US 2013/0063698 A1 Mar. 14, 2013

(30) Foreign Application Priority Data
Sep. 14, 2011 (JP) ................... 2011-200898

(51) Int. Cl.
*A61B 3/14* (2006.01)
*A61B 3/12* (2006.01)
*G06T 5/00* (2006.01)

(52) U.S. Cl.
CPC ............... *A61B 3/12* (2013.01); *G06T 5/004* (2013.01); *G06T 2207/10016* (2013.01); *G06T 2207/10024* (2013.01); *G06T 2207/10048* (2013.01); *G06T 2207/10101* (2013.01); *G06T 2207/20056* (2013.01); *G06T 2207/20224* (2013.01); *G06T 2207/30041* (2013.01)

(58) Field of Classification Search
CPC ....... A61B 3/12; A61B 3/102; A61B 5/14555; A61B 3/14; A61B 3/0025; A61B 3/1225; A61B 5/0066; A61B 5/0073; A61B 5/7257; G06T 2207/30041; G06T 2207/10101; G06T 2207/20224
USPC ........ 351/206, 205, 208, 200, 246; 382/128, 382/131, 103, 130, 284
See application file for complete search history.

(56) References Cited

U.S. PATENT DOCUMENTS

| | | | |
|---|---|---|---|
| 6,377,349 B1 | 4/2002 | Fercher | |
| 7,261,414 B2 | 8/2007 | Saigusa et al. | |
| 7,345,770 B2 | 3/2008 | Chan et al. | |
| 2005/0047638 A1 | 3/2005 | Suzuki et al. | |
| 2008/0021331 A1* | 1/2008 | Grinvald et al. | ............ 600/476 |
| 2009/0136100 A1 | 5/2009 | Shinohara | |
| 2010/0142766 A1 | 6/2010 | Fleming | |

(Continued)

FOREIGN PATENT DOCUMENTS

| | | |
|---|---|---|
| EP | 2064988 A1 | 6/2009 |
| EP | 2179688 A1 | 4/2010 |

(Continued)

OTHER PUBLICATIONS

European Search Report for EP12006033 dated Feb. 28, 2013.
Office action dated Jul. 7, 2015 for JP 2011-200898.

*Primary Examiner* — Huy K Mai
*Assistant Examiner* — Daniele Manikeu
(74) *Attorney, Agent, or Firm* — Pearne & Gordon LLP

(57) ABSTRACT

A fundus observation apparatus according to an embodiment comprises: a photographing part that photographs the fundus of a subject eye; a forming part comprising an optical system that irradiates signal light onto the fundus and interferes reflected light of the signal light from the fundus with reference light via a reference path and detects the resulting interference light, wherein the forming part forms a tomographic image of the fundus based on the detection result; and an analyzing part that analyzes a photographed image of the fundus from the photographing part to delete predetermined low-frequency components from the photographed image.

7 Claims, 8 Drawing Sheets

(56) References Cited

U.S. PATENT DOCUMENTS

| | | |
|---|---|---|
| 2010/0142775 A1 | 6/2010 | Ganeshan et al. |
| 2010/0189334 A1* | 7/2010 | Tomidokoro et al. ........ 382/131 |
| 2011/0080561 A1* | 4/2011 | Hayashi et al. .............. 351/206 |
| 2011/0103655 A1* | 5/2011 | Young ................... G06T 7/0028 382/128 |
| 2011/0228221 A1* | 9/2011 | Hanebuchi et al. .......... 351/206 |
| 2012/0027275 A1* | 2/2012 | Fleming ................ G06F 19/321 382/128 |
| 2012/0065518 A1* | 3/2012 | Mangoubi ................ A61B 3/12 600/473 |
| 2012/0070049 A1* | 3/2012 | Iwase ...................... G06T 7/602 382/128 |
| 2012/0127428 A1* | 5/2012 | Isogai ................... A61B 3/102 351/206 |

FOREIGN PATENT DOCUMENTS

| | | |
|---|---|---|
| JP | 09-276232 A | 10/1997 |
| JP | 11-238129 A | 8/1999 |
| JP | 11-325849 A | 11/1999 |
| JP | 2002-139421 A | 5/2002 |
| JP | 2004-041371 A | 2/2004 |
| JP | 2004-313455 A | 11/2004 |
| JP | 2005-040506 A | 2/2005 |
| JP | 2006-153838 A | 6/2006 |
| JP | 2007-024677 A | 2/2007 |
| JP | 2008-073099 A | 4/2008 |
| JP | 2008-259544 A | 10/2008 |
| JP | 2009-112617 A | 5/2009 |
| JP | 2010-259629 A | 11/2010 |

* cited by examiner

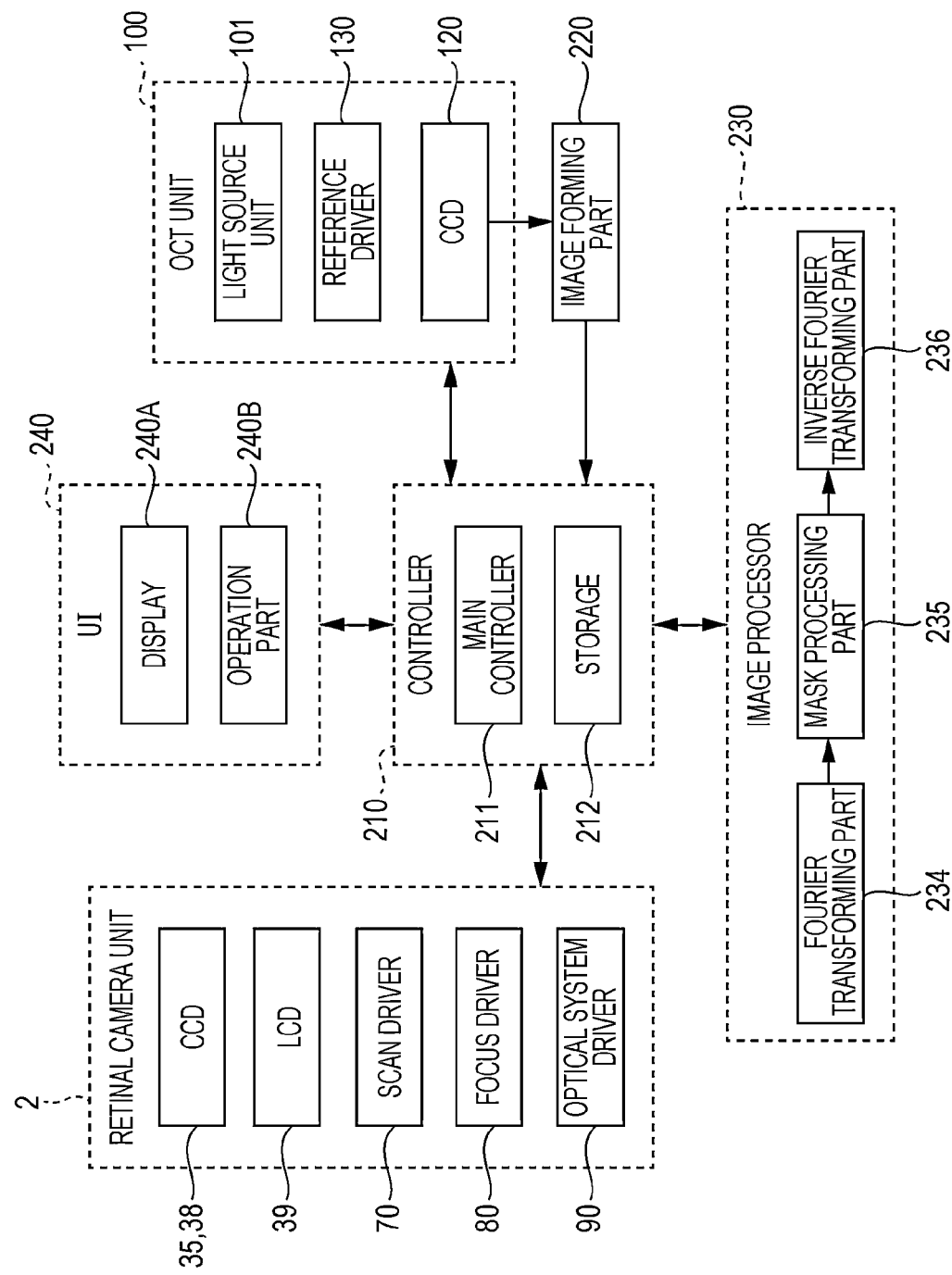

FUNDUS OBSERVATION APPARATUS

TECHNICAL FIELD

The present invention relates to a fundus observation apparatus that forms an image of a fundus by using optical coherence tomography (OCT).

BACKGROUND ART

In recent years, OCT that forms images of the surface morphology and internal morphology of an object by using a light beam from a laser light source or the like has attracted attention. Unlike an X-ray CT apparatus, OCT is noninvasive to human bodies, and is therefore expected to be utilized in the medical field and biological field. For example, in the ophthalmology, apparatuses that form images of a fundus and a cornea are in a practical stage.

Japanese Unexamined Patent Application Publication No. Hei 11-325849 discloses a device to which OCT is applied. This device has such a configuration that: a measuring arm scans an object by a rotary deflection mirror (a Galvano mirror); a reference arm is provided with a reference mirror; and an interferometer is mounted at the outlet to analyze, by a spectrometer, the intensity of an interference light of light fluxes from the measurement arm and the reference arm. Moreover, the reference arm is configured to gradually change the light flux phase of the reference light by discontinuous values.

The device disclosed in Japanese Unexamined Patent Application Publication No. Hei 11-325849 uses a technique of so-called "Fourier Domain OCT." That is to say, the device irradiates a low coherence light beam to an object, superposes the reflected light and the reference light to generate an interference light, and acquires the spectral intensity distribution of the interference light to execute Fourier transform, thereby imaging the morphology in the depth direction (the z-direction) of the object. The technique of this type is also called Spectral Domain.

Furthermore, the device described in Japanese Unexamined Patent Application Publication No. Hei 11-325849 is provided with a Galvano mirror that scans with a light beam (a signal light), and is thereby configured to form an image of a desired measurement target region of the object. This device is configured to scan with the light beam only in one direction (the x-direction) orthogonal to the z-direction. An image formed by this device is a two-dimensional tomographic image in the depth direction (the z-direction) along the scanning direction (the x-direction) of the light beam.

Japanese Unexamined Patent Application Publication No. 2002-139421 discloses a technique of scanning with a signal light in the horizontal direction (x-direction) and the vertical direction (y-direction) to form multiple two-dimensional tomographic images in the horizontal direction, and acquiring and imaging three-dimensional tomographic information of a measured range based on the tomographic images. As the three-dimensional imaging, for example, a method of arranging and displaying multiple tomographic images in the vertical direction (referred to as stack data or the like), and a method of executing a rendering process on volume data (voxel data) based on the stack data to form a three-dimensional image are considered.

Japanese Unexamined Patent Application Publication No. 2007-24677 and Japanese Unexamined Patent Application Publication No. 2006-153838 disclose other types of OCT devices. Japanese Unexamined Patent Application Publication No. 2007-24677 describes an OCT device that images the morphology of an object by scanning (sweeping) the wavelength of light that is irradiated to an object, acquiring the spectral intensity distribution by detecting interference light obtained by superposing the reflected lights of the light of the respective wavelengths on the reference light, and executing Fourier transform. Such an OCT device is called a Swept Source type or the like. The Swept Source type is a kind of the Fourier Domain type.

Further, Japanese Unexamined Patent Application Publication No. 2006-153838 describes an OCT device that irradiates a light having a predetermined beam diameter to an object and analyzes the components of an interference light obtained by superposing the reflected light and the reference light, thereby forming an image of the object in a cross-section orthogonal to the travelling direction of the light. Such an OCT device is called a full-field type, en-face type or the like.

Japanese Unexamined Patent Application Publication No. 2008-73099 discloses a configuration obtained by applying OCT in the ophthalmic field. It should be noted that before the use of OCT, a retinal camera and a slit lamp microscope have been widely used as devices for observing a subject eye (refer to, for example, Japanese Unexamined Patent Application Publication No. Hei 9-276232 and Japanese Unexamined Patent Application Publication No. 2008-259544). The retinal camera is a device that photographs the fundus oculi by projecting illumination light onto the eye and receiving the reflected light from the fundus oculi. The slit lamp microscope is a device that obtains an image of the cross-section of the cornea by cutting off the light section of the cornea using slit light.

A device using OCT is advantageous compared to a retinal camera etc. with respect to the fact that it is capable of acquiring high-definition images, and is also capable of acquiring tomographic images and three-dimensional images.

In this manner, the device using OCT may be applied to the observation of various sites of the subject eye, and because high-resolution images may be obtained, it is applied to the diagnosis of various ophthalmologic diseases.

What is important not only in ophthalmology but to the general medical field is to appropriately image the region of interest. Particularly in ophthalmology, the subject eye, which is the photographing subject, has a very fine structure and accompanies eye movement; therefore, it is not easy to accurately designate the scanning location of a signal light.

Designation of the scanning location is conducted with reference to a real-time moving image (near-infrared fundus image) that uses a near-infrared light. For example, in the OCT measurement of the fundus, there is a method of scanning the fundus with a laser beam in the near-infrared region and imaging a two-dimensional distribution of the reflection intensity from each point (SLO, Scanning Laser Ophthalmoscope) and a method of photographing the fundus lit with a near-infrared light. According to the former, high resolution is achieved by a confocal optical system; however, there is a demerit in that the structure is complicated and expensive. Meanwhile, regarding the latter, it may be achieved by a simple optical system as in conventional retinal cameras; however, because confocality is not used, reflected lights (background components) from optical elements and/or from various depth locations of fundus get mixed, preventing high-resolution such as SLO from being obtained. Accordingly, techniques such as for adjusting the contrast of images, gamma adjustment, etc., are employed (for example, refer to Japanese Unexamined Patent Application Publication No. 2004-41371, Japanese Unexamined Patent Application Publication No. 2004-313455, and Japanese Unexamined Patent Application Publication No. Hei 11-238129).

PRIOR ART DOCUMENTS

Patent Documents

[Patent Document 1]
  Japanese Unexamined Patent Application Publication No. Hei 11-325849
[Patent Document 2]
  Japanese Unexamined Patent Application Publication No. 2002-139421
[Patent Document 3]
  Japanese Unexamined Patent Application Publication No. 2007-24677
[Patent Document 4]
  Japanese Unexamined Patent Application Publication No. 2006-153838
[Patent Document 5]
  Japanese Unexamined Patent Application Publication No. 2008-73099
[Patent Document 6]
  Japanese Unexamined Patent Application Publication No. Hei 9-276232
[Patent Document 7]
  Japanese Unexamined Patent Application Publication No. 2008-259544
[Patent Document 8]
  Japanese Unexamined Patent Application Publication No. 2004-41371
[Patent Document 9]
  Japanese Unexamined Patent Application Publication No. 2004-313455
[Patent Document 10]
  Japanese Unexamined Patent Application Publication No. Hei 11-238129

BRIEF SUMMARY OF THE INVENTION

However, even with the use of these conventional image adjusting techniques, it is difficult to realize sufficient image quality in OCT measurements in the ophthalmologic field. As one of the causes thereof, the conventional technique is a conversion process based on histograms, that is, a conversion process with reference to a look-up table, and therefore the separation of the signal components (reflected light from the plane to be photographed) and the background components cannot be sufficiently performed.

This invention was invented in order to solve the problems mentioned above, with the purpose of providing a fundus observation apparatus that enhances contrast by effectively extracting the signal components from a fundus image such as a near-infrared fundus image etc.

One aspect of the invention is a fundus observation apparatus comprising: a photographing part that photographs the fundus of a subject eye, a forming part comprising an optical system that irradiates signal light onto the fundus and interferes reflected light of the signal light from the fundus with reference light via a reference path and detects the resulting interference light, wherein the forming part forms a tomographic image of the fundus based on the detection result, and an analyzing part that analyzes a photographed image of the fundus from the photographing part to delete predetermined low-frequency components from the photographed image.

Another aspect of the invention is the fundus observation apparatus, wherein the analyzing part comprises: a smoothing part that carries out a smoothing process on the photographed image to form a smoothed image, a difference processing part that forms a difference image between the smoothed image and the photographed image, and a composition processing part that composes the photographed image from the photographing part and the difference image, thereby forming the photographed image with the low-frequency components removed.

Another aspect of the invention is the fundus observation apparatus, wherein the difference processing part multiplies the photographed image and/or the smoothed image by a predetermined weight in order to form the difference image, and the composition processing part conducts the composition by dividing the difference image by a value in which the weight is subtracted from 1.

Another aspect of the invention is the fundus observation apparatus, wherein the weight is a value of 0.7 or more and 0.9 or less, and the difference processing part makes the difference image of the smoothed image multiplied by this value and the photographed image.

Another aspect of the invention is the fundus observation apparatus, wherein the analyzing part comprises: a Fourier transforming part that conducts two-dimensional Fourier transformation on the photographed image and forms an image in a frequency space, a mask processing part that composes a mask image set in advance in the frequency space with the image formed by the Fourier transforming part, and an inverse Fourier transforming part that conducts two-dimensional inverse Fourier transformation on an image formed by the mask processing part to form the photographed image with the low-frequency components removed.

Another aspect of the invention is the fundus observation apparatus, wherein the mask image is a high pass filter that removes the predetermined low-frequency components in the frequency space.

Another aspect of the invention is the fundus observation apparatus, wherein the mask image is a band pass filter that removes the predetermined low-frequency components and the predetermined high-frequency components in the frequency space.

Another aspect of the invention is the fundus observation apparatus, wherein the photographing part forms a moving image of the fundus by repeating the photographing at a specified time interval, the analyzing part analyzes each frame of the moving image and removes the low-frequency components, and further comprising a position adjusting part that adjusts the position of the subject eye and the position of the optical system based on the moving image with the low-frequency components removed.

Another aspect of the invention is the fundus observation apparatus, wherein the photographing part forms a moving image of the fundus by repeating the photographing at a specified time interval, the analyzing part analyzes each frame of the moving image to remove the low-frequency components, the optical system comprises a scanning part that scans the signal light with respect to the fundus, further comprising a setting part that sets the scanning region of the signal light by the scanning part based on the moving image with the low-frequency components removed, and the forming part forms a tomographic image based on the detection results of the interference light based on the signal light to the set scanning region.

Another aspect of the invention is the fundus observation apparatus further comprising a specifying part that analyzes the photographed image with the low-frequency components removed to specify a distinctive site in the photographed image.

Another aspect of the invention is the fundus observation apparatus further comprising a determining part that analyzes the photographed image with the low-frequency components removed to determine the image quality of the photographed image.

Another aspect of the invention is the fundus observation apparatus, wherein the optical system comprises a scanning part that two-dimensionally scans the signal light with respect to the fundus, the forming part forms multiple tomographic images based on the detection results obtained by the two-dimensional scanning, forms a three-dimensional image based on the multiple tomographic images, and forms a projection image by projecting the three-dimensional image in the depth direction of the fundus, and further comprising an image position adjusting part that adjusts the position of the projection image and the position of the photographed image with the low-frequency components removed.

According to this invention, predetermined low-frequency components may be removed from the photographed image by the photographing part; consequently, the signal components may be efficiently extracted from the fundus image, enhancing the contrast.

BRIEF DESCRIPTION OF THE DRAWINGS

FIG. 6 is a schematic block diagram showing an example of a configuration of an embodiment of a fundus observation apparatus according to the present invention.

MODE FOR CARRYING OUT THE INVENTION

An example of an embodiment of a fundus observation apparatus according to the present invention will be described in detail with reference to the drawings. The fundus observation apparatus according to the present invention forms a tomographic image and a three-dimensional image of a fundus using optical coherence tomography. It should be noted that an image obtained by optical coherence tomography is sometimes referred to as an OCT image. Furthermore, a measuring action for forming an OCT image is sometimes referred to as an OCT measurement.

In the following embodiments, a configuration to which an OCT of the Fourier-Domain type is applied will be described in detail. To be specific, similar to a device disclosed in Japanese Unexamined Patent Application Publication No. 2008-73099, a fundus observation apparatus according to the embodiment is capable of obtaining both OCT images of a fundus and fundus images. It should be noted that it is also possible to apply a configuration of the present invention to a fundus observation apparatus to which an OCT of the type other than Fourier-Domain is applied.

Embodiment 1

Configuration

Figure 1:
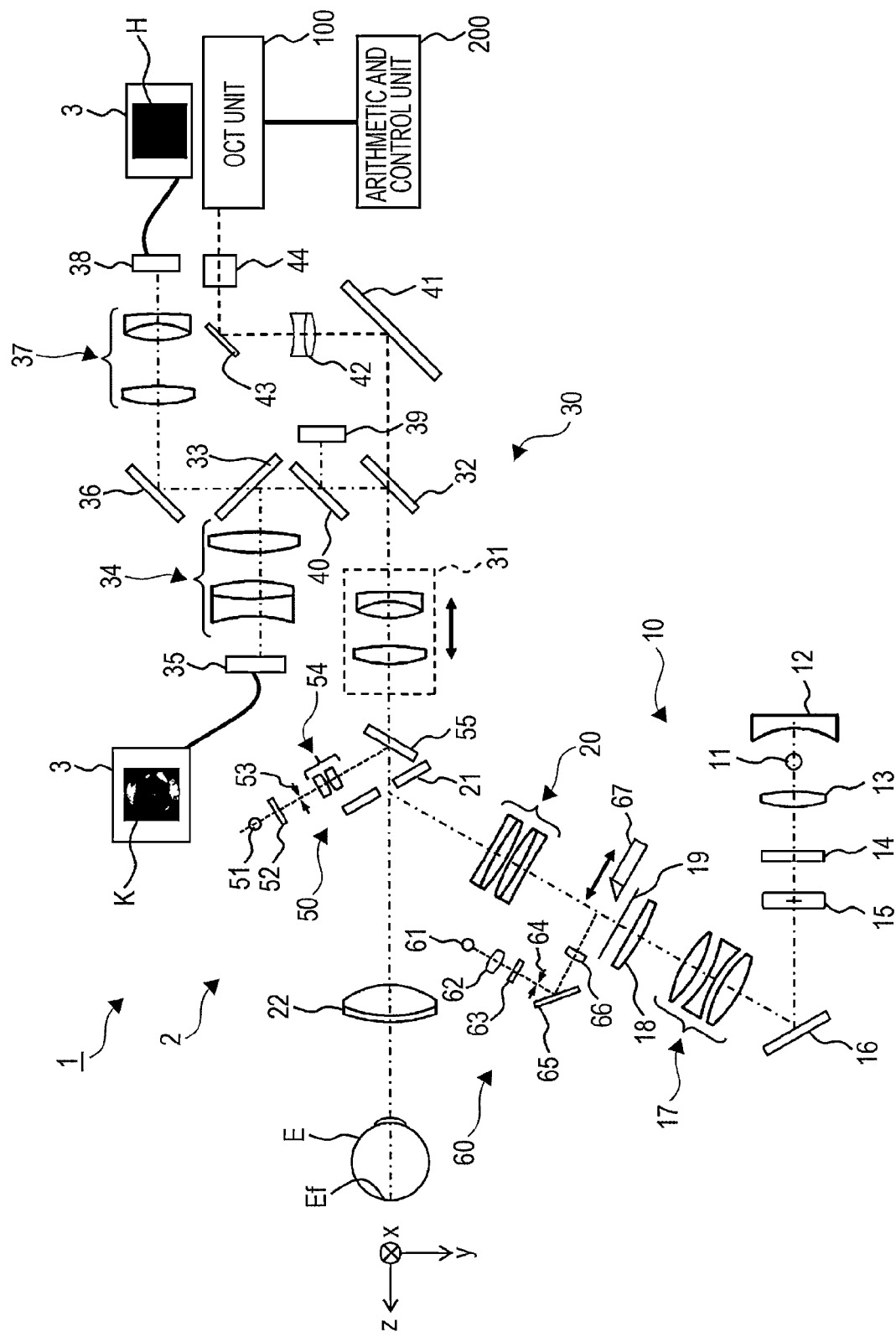
FIG. 1 is a schematic view showing an example of a configuration of an embodiment of a fundus observation apparatus according to the present invention.
Figure 2:
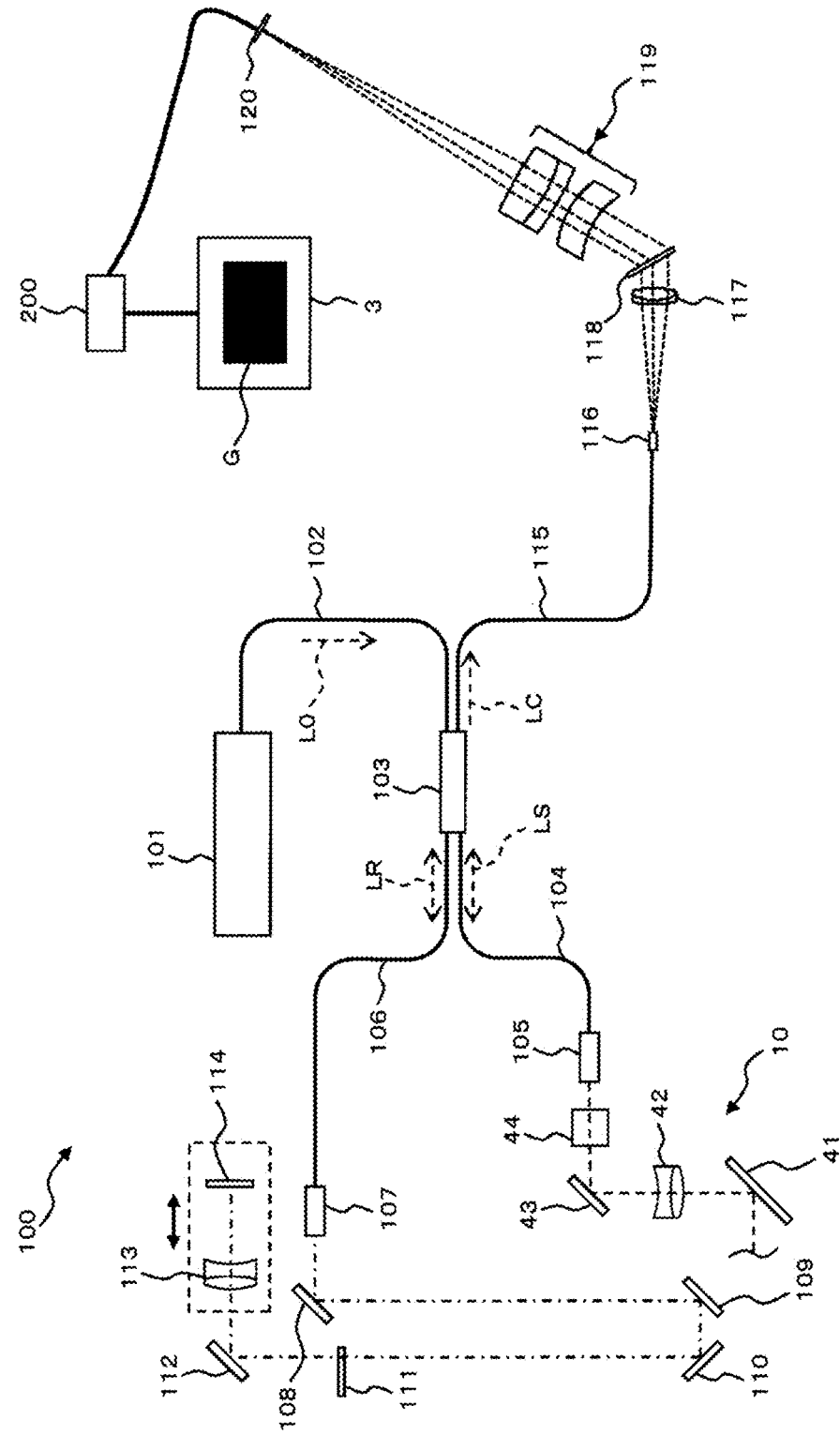
FIG. 2 is a schematic view showing an example of a configuration of an embodiment of a fundus observation apparatus according to the present invention.

A fundus observation apparatus 1, as shown in FIG. 1 and FIG. 2, includes a retinal camera unit 2, an OCT unit 100, and an arithmetic and control unit 200. The retinal camera unit 2 has almost the same optical system as a conventional retinal camera. The OCT unit 100 is provided with an optical system for obtaining an OCT image of a fundus. The arithmetic and control unit 200 is provided with a computer that executes various arithmetic processes, control processes, and so on.

[Retinal Camera Unit]

The retinal camera unit 2 shown in FIG. 1 is provided with an optical system for forming a two-dimensional image (fundus image) representing the surface morphology of the fundus Ef of a subject eye E. Fundus images include observation images, captured images, etc. The observation image is, for example, a monochrome moving image formed at a prescribed frame rate using near-infrared light. The captured image is, for example, a color image captured by flashing visible light, or a monochrome still image using near-infrared light or visible light as illumination light. The retinal camera unit 2 may be configured to be capable of acquiring other types of images such as a fluorescein angiography image, an indocyanine green fluorescent image and a fundus autofluorescent image. It should be noted that an arbitrary type of image photographed by using infrared light corresponds to the "photographed image" of the present invention. Furthermore, the retinal camera unit 2 is an example of the "photographing part" of the present invention.

The retinal camera unit 2 is provided with a chin rest and a forehead placement for retaining the face of the subject. Moreover, the retinal camera unit 2 is provided with an illumination optical system 10 and an imaging optical system 30. The illumination optical system 10 irradiates an illumination light to the fundus Ef. The imaging optical system 30 guides a fundus reflected light of the illumination light to imaging devices (CCD image sensors (sometimes simply called CCD) 35, 38). Moreover, the imaging optical system 30 guides a signal light coming from the OCT unit 100 to the fundus Ef, and guides the signal light propagated through the fundus Ef to the OCT unit 100.

An observation light source 11 of the illumination optical system 10 comprises, for example, a halogen lamp. Light (observation illumination light) output from the observation light source 11 is reflected by a reflection mirror 12 with a curved reflection surface, and becomes near-infrared after passing through a visible cut filter 14 via a condenser lens 13. Furthermore, the observation illumination light is once converged near an imaging light source 15, reflected by a mirror 16, and passes through relay lenses 17, 18, diaphragm 19, and relay lens 20. Then, the observation illumination light is reflected on the peripheral part (the surrounding region of an aperture part) of an aperture mirror 21 and illuminates the fundus Ef via an object lens 22.

The fundus reflection light of the observation illumination light is refracted by the object lens 22, passes through the aperture part formed in the center region of the aperture mirror 21, passes through a dichroic mirror 55 and, travels through a focusing lens 31, and is reflected by a dichroic mirror 32. Furthermore, the fundus reflection light passes through a half-mirror 40 and forms an image on the light receiving surface of the CCD image sensor 35 by a condenser lens 34 after being reflected by a dichroic mirror 33. The CCD image sensor 35 detects, for example, the fundus reflection light at a prescribed frame rate. An image (observation image) K based on the fundus reflection light detected by the CCD image sensor 35 is displayed on a display device 3. It should be noted that when the focus of the imaging optical system 30 is adjusted to the anterior eye part, an observation image K of the anterior eye part of the subject eye E is displayed.

The imaging light source 15 consists of, for example, a xenon lamp. The light (imaging illumination light) output from the imaging light source 15 is irradiated to the fundus Ef via a route that is similar to the observation illumination light. The fundus reflection light of the imaging illumination light is guided to the dichroic mirror 33 via the same route as that of the observation illumination light, passes through the dichroic mirror 33, and forms an image on the light receiving surface of the CCD image sensor 38 by a condenser lens 37 after being reflected by a mirror 36. An image (captured image) H based on the fundus reflection light detected by the CCD image sensor 38 is displayed on the display device 3. It should be noted that the display device 3 for displaying an observation image K and the display device 3 for displaying a captured image H may be the same or different. Furthermore, when similar photographing is carried out by illuminating the subject eye E with infrared light, an infrared captured image H is displayed.

An LCD (Liquid Crystal Display) 39 displays a fixation target or a visual target for measuring eyesight. The fixation target is a visual target for fixing the subject eye E, and is used when photographing a fundus or OCT measurement.

Part of the light output from the LCD 39 is reflected by a half-mirror 40, reflected by the dichroic mirror 32, passes through the aperture part of the aperture mirror 21 via the focusing lens 31 as well as a dichroic mirror 55, is refracted by the object lens 22 and projected to the fundus Ef.

By changing a display position of the fixation target on the screen of the LCD 140, it is possible to change a fixation position of the subject eye E. As the fixation position of the subject eye E, there are a position for acquiring an image centered on the macula of the fundus Ef, a position for acquiring an image centered on the optic papilla, a position for acquiring an image centered on the fundus center between the macula and the optic papilla, and so on, for example, as in conventional retinal cameras.

Furthermore, as with conventional retinal cameras, the retinal camera unit 2 is provided with an alignment optical system 50 and a focus optical system 60. The alignment optical system 50 generates a target (alignment target) for matching the position (alignment) of the device optical system with respect to the subject eye E. The focus optical system 60 generates a target (split target) for matching the focus with respect to the subject eye E.

Light (alignment light) output from the LED (Light Emitting Diode) 51 of the alignment optical system 50 is reflected by the dichroic mirror 55 via diaphragms 52, 53 and a relay lens 54, passes through the aperture part of the aperture mirror 21, and is projected onto the cornea of the subject eye E by the object lens 22.

Part of cornea reflection light of the alignment light is transmitted through the dichroic mirror 55 via the object lens 22 and the aperture part, passes through the focusing lens 31, is reflected by the dichroic mirror 32, transmitted through the half-mirror 40, reflected by the dichroic mirror 33, and projected onto the light receiving surface of the CCD image sensor 35 by the condenser lens 34. An image (alignment target) captured by the CCD image sensor 35 is displayed on the display device 3 along with the observation image K. A user conducts alignment by an operation that is the same as conventional retinal cameras. It should be noted that alignment (auto-alignment) may be performed, by an arithmetic and control unit 200, as a result of analyzing the position of the alignment target and moving the optical system.

In order to conduct focus adjustment, the reflection surface of a reflection rod 67 is provided in a slanted position on the light path of the illumination optical system 10. Light (focus light) output from an LED 61 of the focus optical system 60 passes through a relay lens 62, is split into two light fluxes by a split target plate 63, passes through a two-hole diaphragm 64, is reflected by a mirror 65, and is reflected after an image is formed once on the reflection surface of the reflection rod 67 by a condenser lens 66. Furthermore, the focus light is reflected at the aperture mirror 21 via the relay lens 20 and an image is formed on the fundus Ef by the object lens 22.

The fundus reflection light of the focus light passes through the same route as the cornea reflection light of the alignment light and is detected by the CCD image sensor 35. A light (split target) captured by the CCD image sensor 35 is displayed on the display device 3 along with an observation image K. The arithmetic and control unit 200, as in the past, analyzes the position of the split target, and moves the focusing lens 31 and the focus optical system 60 for focusing (auto-focusing). It should be noted that focusing may be performed manually while visually recognizing the split target.

An optical path including a mirror 41, collimator lens 42, and Galvano mirrors 43, 44 is provided behind the dichroic mirror 32. The optical path is guided to the OCT unit 100.

The Galvano mirror 44 performs scanning with a signal light LS from the OCT unit 100 in the x-direction. The Galvano mirror 43 performs scanning with a signal light LS in the y-direction. Scanning may be performed with the signal light LS in an arbitrary direction in the xy-plane due to the two Galvano mirrors 43 and 44.

[OCT Unit]

The OCT unit 100 is provided with an optical system for obtaining an OCT image of the fundus Ef (see FIG. 2). The optical system has a similar configuration to a conventional Fourier-Domain-type OCT device. That is to say, the optical system is configured to split light from an light source into a reference light and a signal light, make the signal light propagated through a fundus and the reference light propagated through a reference optical path interfere with each other to generate an interference light, and obtains the spectral component of this interference light. This detection result (detection signal) is transmitted to the arithmetic and control unit 200.

The light source unit 101 outputs a broadband, low-coherence light L0. The low-coherence light L0 includes, for example, a near-infrared waveband (approximately 800 nm to 900 nm), and has a temporal coherence length of around several tens of micrometers. Furthermore, a waveband that is not visible to the human eye, such as near-infrared light with a central wavelength of around 1040 to 1060 nm, for example, may be used as the low-coherence light L0.

The light source unit 101 is configured to include light output device, such as an SLD (super luminescent diode), LED, SOA (Semiconductor Optical Amplifier) and the like. Moreover, in this embodiment, the spectral domain type in particular is explained; however, when applying a swept source type, the laser light source allowing sweeping of the wavelength is used as the light source unit 101. Generally, as the configuration of the light source unit 101, those corresponding to the type of optical coherence tomography are appropriately selected.

The low coherence light L0 output from the light source unit 101 is guided to a fiber coupler 103 by an optical fiber 102 and split into signal light LS and reference light LR.

The signal light LS is guided by the optical fiber 104 and becomes a parallel light flux by a collimator lens unit 105. Furthermore, the signal light LS is reflected by Galvano mirrors 44 and 43, converged by the collimator lens 42, reflected by the mirror 41, transmitted through a dichroic mirror 32, and irradiated to the fundus Ef after passing through a route that is the same as the light from the LCD 39. The signal light LS is scattered and reflected at the fundus Ef. The scattered light and the reflection light are sometimes all together referred to as the fundus reflection light of the signal light LS. The fundus reflection light of the signal light LS progresses along the same route in the reverse direction and is guided to the fiber coupler 103.

The reference light LR is guided by an optical fiber 106 and becomes a parallel light flux by a collimator lens unit 107. Furthermore, the reference light LR is reflected by mirrors 108, 109, 110, dimmed by an ND (Neutral Density) filter 111, and reflected by a mirror 112, with the image formed on a reflection surface of a reference mirror 114 by a collimator lens 113. The reference light LR reflected by the reference mirror 114 progresses along the same route in the reverse direction and is guided to the fiber coupler 103. It should be noted that an optical element for dispersion compensation (pair prism, etc.) and/or an optical element for polarization correction (wave plate, etc.) may also be provided for the optical path (reference optical path) of the reference light LR.

The fiber coupler 103 superposes the fundus reflection light of the signal light LS and the reference light LR reflected by the reference mirror 114. Interference light LC thus generated is guided by an optical fiber 115 and output from an exit end 116. Furthermore, the interference light LC is converted to a parallel light flux by a collimator lens 117, spectrally divided (spectrally decomposed) by a diffraction grating 118, converged by the convergence lens 119, and projected onto the light receiving surface of a CCD image sensor 120. Although the diffraction grating 118 shown in FIG. 2 is of the transmission type, it is possible to use the reflection type.

The CCD image sensor 120 is for example a line sensor, and detects the respective spectral components of the spectrally decomposed interference light LC and converts the components into electric charges. The CCD image sensor 120 accumulates these electric charges and generates a detection signal. Furthermore, the CCD image sensor 120 transmits the detection signal to the arithmetic and control unit 200.

Although a Michelson-type interferometer is employed in this embodiment, it is possible to employ any type of interferometer such as a Mach-Zehnder-type as necessary. Instead of a CCD image sensor, other types of image sensors, such as a CMOS (Complementary Metal Oxide Semiconductor) image sensor, can be used.

[Arithmetic and Control Unit]

A configuration of the arithmetic and control unit 200 will be described. The arithmetic and control unit 200 analyzes the detection signals inputted from the CCD image sensor 120, and forms an OCT image of the fundus Ef. An arithmetic process for this is the same as that of a conventional Fourier-Domain-type OCT device.

Further, the arithmetic and control unit 200 controls each part of the retinal camera unit 2, the display device 3 and the OCT unit 100. For example, the arithmetic and control unit 200 causes the display device 3 to display a tomographic image G of the fundus Ef (see FIG. 2).

Moreover, as control of the retinal camera unit 2, the arithmetic and control unit 200 executes: control of action of the observation light source 101, the imaging light source 103 and LED's 51 and 61; control of action of the LCD 39; control of movement of the focusing lens 31; control of movement of the reflection rod 67; control of movement of the focus optical system 60; control of action of the respective Galvano mirrors 43 and 44; and so on.

Further, as control of the OCT unit 100, the arithmetic and control unit 200 executes: control of action of the light source unit 101; control of movement of the reference mirror 114 and the collimator lens 113; control of action of the CCD image sensor 120; and so on.

The arithmetic and control unit 200 includes a microprocessor, a RAM, a ROM, a hard disk drive, a communication interface, and so on, as in conventional computers. The storage device such as the hard disk drive stores a computer program for controlling the fundus observation apparatus 1. The arithmetic and control unit 200 may be provided with a circuit board dedicated for forming OCT images based on detection signals from the CCD image sensor 120. Moreover, the arithmetic and control unit 200 may be provided with operation devices (input devices) such as a keyboard and a mouse, and/or display devices such as LCD.

The retinal camera unit 2, display device 3, OCT unit 100, and arithmetic and control unit 200 may be integrally configured (that is, within a single case), or configured as separate bodies.

[Control System]

Figure 3:
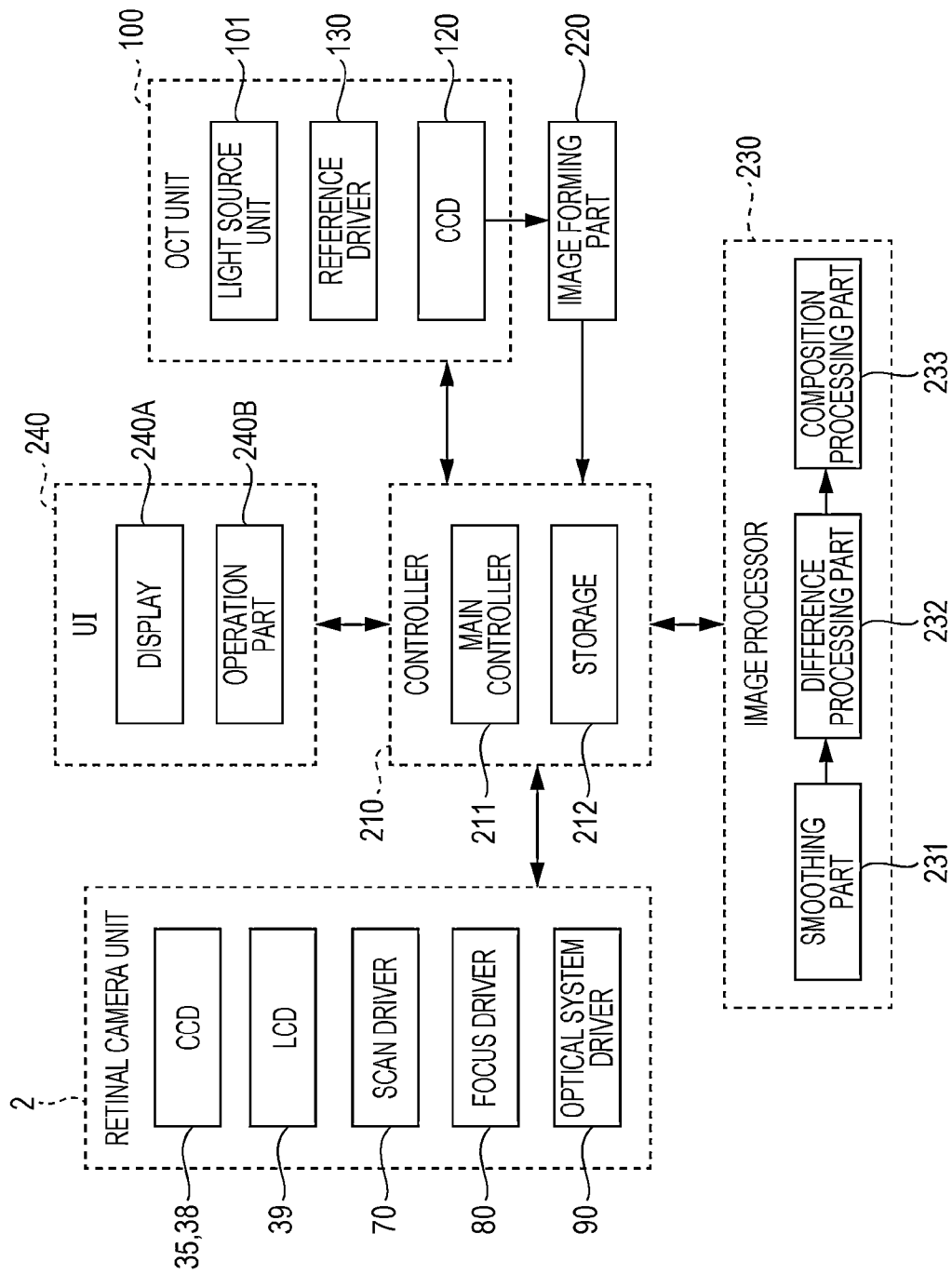
FIG. 3 is a schematic block diagram showing an example of a configuration of an embodiment of a fundus observation apparatus according to the present invention.

A configuration of a control system of the fundus observation apparatus 1 will be described with reference to FIG. 3.

(Controller)

The control system of the fundus observation apparatus 1 has a configuration centered on a controller 210. The controller 210 includes, for example, the aforementioned microprocessor, RAM, ROM, hard disk drive, and communication interface. The controller 210 is provided with a main controller 211 and storage 212.

(Main Controller)

The main controller 211 performs the aforementioned various kinds of control. Specifically, the main controller 211 controls a scan driver 70, a focus driver 80 and an optical system driver 90 of the retinal camera unit 2, and further controls the light source unit 101 and a reference driver 130 of the OCT unit 100.

The scan driver 70 independently changes the orientations of the Galvano mirrors 43 and 44. The focus driver 80 moves the focusing lens 31 in the optical axis direction. Thereby, the focus position of the imaging optical system 30 is changed. The optical system driver 90 three-dimensionally moves the optical system provided in the retinal camera unit 2. The reference driver 130 integrally moves the collimator lens 113 as well as the reference mirror 114 along the travelling direction of the reference light LR.

The main controller 211 executes a process of writing data into the storage 212, and a process of reading out data from the storage 212.

The storage 212 stores various kinds of data. The data stored in the storage 212 is, for example, image data of OCT images, image data of fundus images, and eye information. The eye information includes information on a subject such as a patient ID and a name, information on the subject eye such as information on identification of left eye or right eye, and so on. Moreover, various types of data in order to operate the fundus observation apparatus 1 are stored in the storage 212.

(Image Forming Part)

An image forming part 220 forms image data of a tomographic image of the fundus Ef based on the detection signals from the CCD image sensor 120. Like the conventional Fourier-Domain OCT, this process includes processes such as noise elimination (noise reduction), filtering, dispersion correction and FFT (Fast Fourier Transform). The image forming part 220 functions as the "forming part" together with an optical system used in OCT measurement.

The image forming part 220 includes, for example, the aforementioned circuit board. It should be noted that "image data" and the "image" presented based on the image data may be identified with each other in this specification.

(Image Processor)

An image processor 230 executes various image processing and analysis on images formed by the image forming part 220. For example, the image processor 230 executes various correction processes such as luminance correction of images.

The image processor 230 executes known image processes such as an interpolation process of interpolating pixels between tomographic images, thereby forming image data of a three-dimensional image of the fundus Ef. Image data of a three-dimensional image refers to image data that the positions of pixels are defined by the three-dimensional coordinates. The image data of a three-dimensional image is, for example, image data composed of three-dimensionally arranged voxels. This image data is referred to as volume data, voxel data, or the like. For displaying an image based on the volume data, the image processor 230 executes a rendering process (such as volume rendering and MIP (Maximum Intensity Projection)) on this volume data, and forms image data of a pseudo three-dimensional image taken from a specific view direction. On a display device such as the display 240A, this pseudo three-dimensional image is displayed.

Further, it is also possible to form stack data of multiple tomographic images as the image data of a three-dimensional image. Stack data is image data obtained by three-dimensionally arranging multiple tomographic images obtained along multiple scanning lines, based on the positional relation of the scanning lines. That is to say, stack data is image data obtained by expressing multiple tomographic images defined by originally individual two-dimensional coordinate systems by a three-dimensional coordinate system (namely, embedding into a three-dimensional space).

The image processor 230 functions as an analyzing part that analyzes the fundus image obtained from photographing using an infrared light to remove the predetermined low-frequency components of the fundus image. The low-frequency components removal process will be explained. Light detected by the retinal camera unit 2 contains not only the surface reflected light (signal components) of the fundus Ef but also the reflected light, etc. (background components) from optical elements included in the optical system. Moreover, the signal components are relatively small while the background components are relatively large. Therefore, by subtracting the background components from the fundus image, the component not involved in imaging of the surface morphology of the fundus Ef, which is the purpose, may be removed. Generally, because the reflected light from sites other than the fundus Ef is not focused on the light receiving surface of the CCD image sensors 35 and 38, this reflected light becomes the low-frequency components (defocused components) of the fundus image. In this embodiment, such low-frequency components are removed from the fundus image. Moreover, a living eye is substantially always moving due to eye movements such as involuntary eye movement during fixation, flicks, etc., so the background components cannot be effectively specified beforehand. Accordingly, it is necessary to analyze the obtained fundus image itself in order to remove the background components.

In order to realize such processing, the image processor 230 is provided with a smoothing part 231, a difference processing part 232, and a composition processing part 233. Moreover, the image processor 230 or the retinal camera unit 2 conducts the process of converting an image signal from the CCD image sensors 35 and 38 into a digital signal in the same manner as a general digital camera. The digital signal is temporarily stored in, for example, a frame memory (not illustrated), and is served in processes of the smoothing part 231 and the subsequent parts.

(Smoothing Part)

The smoothing part 231 conducts smoothing processing on the fundus image. The image made in this manner is referred to as a smoothed image. As the smoothing process, any technique such as a moving average filtering process, Gaussian filtering process, various spatial filtering processes, down sampling, etc., may be applied.

(Difference Processing Part)

The difference processing part 232 conducts difference processing of the smoothed image and the original fundus image. The image made thereby is referred to as a difference image. By the difference process, areas depicted relatively clearly in the original fundus image such as blood vessels and a contour of optic disc in the fundus Ef, that is, the high-frequency components of the original fundus image are extracted.

Before conducting the difference process, it is possible to multiply the smoothed image and/or the original fundus image by a prescribed weight. As an example, the difference processing part 232 forms the difference image by multiplying the smoothed image by a weight w (for example, a value 0.7 or more and 0.9 or less), and subtracting the smoothed image multiplied by the weight w from the original fundus image. It should be noted that the weight w can be set appropriately according to the method and degree of gradations. For example, the weight w may be a value set in advance or may be a value calculated based on the degree of defocus in the original fundus image.

(Composition Processing Part)

The composition processing part 233 the fundus image (composed image) with the low-frequency components removed from the original fundus image by composing the original fundus image and the difference image. The composition process is, for example, an adding process. As mentioned above, the composed image is an image in which the predetermined low-frequency components are removed from the original fundus image.

The image processor 230 may conduct various image processes such as intensity adjustment on the composed image made by the composition processing part 233 in order to attempt enhancement of image quality (contrast, etc.). Hereinafter, images in which such image processing is conducted are also referred to as composed images.

The image processor 230 that functions as above includes, for example, the aforementioned microprocessor, RAM, ROM, hard disk drive, circuit board, and so on. Computer programs that cause a microprocessor to execute the above functions are previously stored in a storage device such as a hard disk drive.

(User Interface)

A user interface 240 includes the display 240A and the operation part 240B. The display 240A is configured including the aforementioned display device of arithmetic and control unit 200 and the display device 3. The operation part 240B is configured including the aforementioned operation device of arithmetic and control unit 200. The operation part 240B may also include various kinds of buttons or keys provided with the case of the fundus observation apparatus 1 or its outside. For example, if the retinal camera unit 2 has a case that is the same as conventional retinal cameras, a joy stick, operation panel, etc. provided on the case may also be included in the operation part 240B. Furthermore, the display 240A may also include various display devices such as a touch panel monitor, etc. provided on the case of the retinal camera unit 2.

The display 240A and the operation part 240B do not need to be composed as separate devices. For example, like a touch panel LCD, a device in which the display function and the operation function are integrated can be used.

[Scan with Signal Light and OCT Image]

A scan with the signal light LS and an OCT image will be described.

The scanning patterns of the signal light LS by the fundus observation apparatus 1 is, for example, a horizontal scan, vertical scan, cruciform scan, radial scan, circular scan, concentric scan, and helical scan. These scanning patterns are selectively used as necessary in consideration of an observation site of the fundus, an analysis target (the retinal thickness or the like), a time required to scan, the accuracy of a scan, and so on.

A horizontal scan is a scan with the signal light LS in the horizontal direction (x-direction). The horizontal scan includes an aspect of scanning with the signal light LS along multiple scanning lines extending in the horizontal direction arranged in the vertical direction (y-direction). In this aspect, it is possible to set any interval between scanning lines. By setting the interval between adjacent scanning lines to be sufficiently narrow, it is possible to form the aforementioned three-dimensional image (three-dimensional scan). A vertical scan is also performed in a similar manner.

A cruciform scan is a scan with the signal light LS along a cross-shape trajectory formed by two linear trajectories (line trajectories) orthogonal to each other. A radial scan is a scan with the signal light LS along a radial trajectory formed by multiple line trajectories arranged at predetermined angles. The cruciform scan is an example of the radial scan.

A circular scan is a scan with the signal light LS along a circular trajectory. A concentric scan is a scan with the signal light LS along multiple circular trajectories arranged concentrically around a predetermined center position. The circular scan is regarded as a special example of the concentric scan. A helical scan is a scan with the signal light LS along a helical trajectory while making the turning radius gradually smaller (or greater).

Because the galvano mirrors 43, 44 are configured to scan the signal light LS in mutually perpendicular directions, it is possible to independently scan the signal light LS in the x-direction and the y-direction. Furthermore, by simultaneously controlling the orientations of the galvano mirrors 43, 44, it is possible to scan the signal light LS along any trajectory on the xy plane. As a result, various scanning patterns such as those described above may be realized.

By scanning the signal light LS in the mode described above, it is possible to form tomographic images of a cross-section (xz plane) in the depth direction of the fundus (z-direction) along scanning lines (scan trajectory). Moreover, in a case that the interval between scanning lines is narrow, it is possible to form the aforementioned three-dimensional image.

A region on the fundus Ef subjected to scanning by the signal light LS as above, that is a region of the fundus Ef subject to OCT measurement, is referred to as a scanning region. A scanning region in three-dimensional scanning is a rectangular-shaped region in which multiple horizontal scans are arranged. Furthermore, a scanning region in a concentric circular scan is a disc-shaped region surrounded by the trajectories of a circular scan of a maximum diameter. Moreover, the scanning region in a radial scan is a disc-shaped (or polygonal-shaped) region linking end positions of scanning lines.

OPERATIONS

Operations of the fundus observation apparatus 1 will be described.

Operation Example 1

Figure 4:
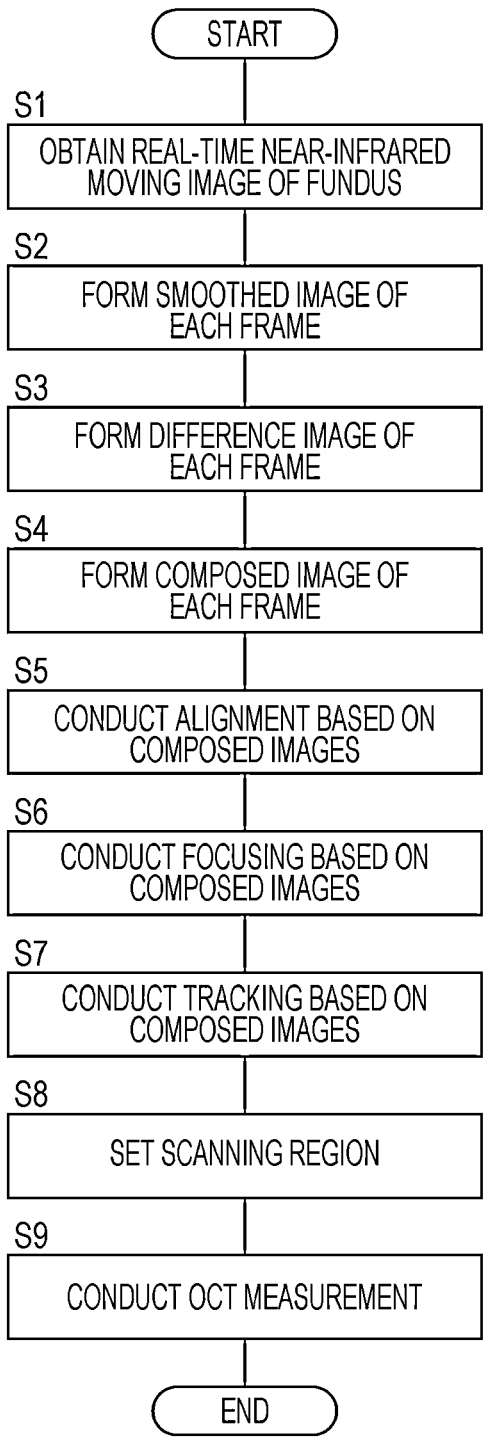
FIG. 4 is a flowchart showing an example of an action of an embodiment of a fundus observation apparatus according to the present invention.

FIG. 4 shows an example of the operation of the fundus observation apparatus 1. In this operation example, OCT measurement performed by utilizing the composed image made by the image processor 230 is explained. This operation example includes the position adjusting process between the subject eye E and the device optical system based on the composed image, along with a setting process of the scanning region based on the composed image.

The position adjusting process contains, for example, an alignment for OCT measurement (auto-alignment), focusing (auto-focusing), and tracking (auto-tracking). Tracking is an operation that moves the device optical system in accordance with the eye movement of the subject eye E. Alignment and focusing are conducted before tracking. Tracking is a function that maintains a positional relationship in which alignment and focus are suitable, by having the location of the device optical system track the eye movement.

(S1: Obtain Real-Time Near-Infrared Moving Image)

First, the near-infrared moving image of the fundus Ef is obtained by continuously lighting the fundus Ef with illumination light (the near-infrared light by the visible cut filter 14) from the observational light source 11. The near-infrared moving image is obtained in real time until the continuous illumination terminates. Each still image (frame) configuring the moving image is temporarily stored in the frame memory (storage 212) and is successively sent to the image processor 230.

At this time, an alignment target by the alignment optical system 50 and a split target by the focus optical system 60 are projected onto the subject eye E. Therefore, the alignment target and the split target are depicted in the near-infrared moving image. Moreover, the fixation target by LCD 39 is also projected. The subject is instructed to stare at the fixation target.

(S2: Smoothing Process)

The smoothing part 231 conducts smoothing processing on the frame successively input from the controller 210 to form the smoothed image of each frame, and successively inputs the smoothed image to the difference processing part 232.

(S3: Difference Process)

The difference processing part 232 successively forms the difference image between the smoothed images successively input from the smoothing part 231 and the frames that are bases of the smoothed images. Then, the difference processing part 233 successively inputs the successively formed difference images into the composition processing part 233.

(S4: Composition Process)

The composition processing part 233 successively forms the composed images of the difference images successively input from the difference processing part 232 and the original frames of the difference images. Then, the composition processing part 233 successively inputs the successively formed composed images into the controller 210.

(S5, S6: Auto-Alignment, Auto-Focusing)

The controller 210 conducts auto-alignment by controlling the optical system driver 90 based on the alignment target depicted in the composed images successively input from the image processor 230. Moreover, the controller 210 conducts auto-focusing by controlling the focus driver 80 based on the split target depicted in the composed images successively input from the image processor 230.

(S7: Auto-Tracking)

Next, the controller 210 commences auto-tracking based on the composed images successively input from the image processor 230. More concretely, the controller 210 specifies the distinctive site (optic disc, blood vessel, lesion site, etc.) of the fundus Ef depicted in each composed image, and controls the optical system driver 90 so that the location (coordinate) of the distinctive site in the frame is constant among the composed images. Thereby, movement of the images in the frames caused by eye movement is suppressed, depicting the distinctive site in substantially the same location within the frame.

(S8: Set Scanning Region)

The controller 210 causes the display part 240A to display, in real time, the near-infrared moving image in which auto-tracking is currently carried out. The user sets a scanning region in the near-infrared moving image by using the operating part 240B. The scanning region may be a one-dimensional region or a two-dimensional region.

Furthermore, when the scanning mode of the signal light LS and/or sites of interest (optic disc, macula, lesion site, etc.) are set in advance, etc., a configuration may be taken such that the controller 210 sets the scanning region based on these settings and the composed images.

Moreover, when setting the same scanning region as the OCT measurement conducted in the past (so-called follow-up), the controller 210 may reproduce the past scanning region upon a real time near-infrared moving image. As a detailed example thereof, the controller 210 associates information (scanning mode, etc.) showing the scanning region set in a past test with the near-infrared fundus image (still image, for example, it may be a frame) in which the scanning region is set and stored in the storage 212 (it is also associated with the patient ID and information of the left and right eye upon actual use). The controller 210 conducts the image position adjusting process between the past near-infrared fundus image and the frame of the current near-infrared moving image, and specifies the image region in the current near-infrared moving image corresponding to the scanning region in the past near-infrared fundus image. Thereby, the scanning region adopted in past tests is set with respect to the current near-infrared moving image.

(S9: OCT Measurement)

The controller 210 controls the light source unit 101 and the reference driver 130 in addition to controlling the scan driver 70 based on the scanning region set in step 8, thereby, conducting OCT measurement of the fundus Ef. The image forming part 220 forms a tomographic image of the fundus Ef based on the obtained detection signals. When the scanning mode is a three-dimensional scan, the image processor 230 forms a three-dimensional image of the fundus Ef based on multiple tomographic images made by the image forming part 220. This concludes the operation example.

It should be noted that, in Steps 7 and 8 mentioned above, the near-infrared moving image in which auto-tracking is carried out is displayed and the scanning region is set in the near-infrared moving image; however, the setting mode of the scanning regions is not limited to this. For example, together with displaying the composed image of one frame of the near-infrared moving image (referred to as a standard composed image), auto-tracking is carried out in the background thereof. When the scanning region is set on the standard composed image, the controller 210 executes image position adjusting process between the standard composed image and the composed image currently served in auto-tracking, thereby specifying the image region in the real-time near-infrared moving image corresponding to the scanning region set in the standard composed image. With this processing as well, the scanning region may be set in the real-time near-infrared moving image in the same manner as Steps 7 and 8 mentioned above. Furthermore, according to this method, the scanning region may be set in the still image, so making the operation simple and certain may be strived for more than in the case of setting on a moving image in which auto-tracking is currently carried out.

In this operation example, the controller 210, alignment optical system 50, focus optical system 60, focus driver 80, optical system driver 90, etc. function as a "position adjusting part." Moreover, galvanometer mirrors 43 and 44 as well as the scan driver 70 function as a "scanning part," and the controller 210 functions as a "setting part."

Operation Example 2

The image processor 230 analyzes the composed image obtained by removing the low-frequency components from the near-infrared fundus image, thereby specifying the distinctive site in the composed image. As the distinctive site, there is a fundus tissue and a lesion site. As the fundus tissue, there are an optic disc, a macula, blood vessels, etc. This distinctive site specifying process is realized by various image processes based on the brightness of the image in the same manner as is conventional. The image processor 230 of this operation example functions as a "specifying part."

Moreover, the image processor 230 can determine the name, presence, and degree of the lesion based on a specified distinctive site. As a detailed example thereof, information to determine the names, presence, and degrees of lesions is stored in the storage 212 in advance. In this information, for example, the characteristics of each disease statistically obtained from multiple clinical data are stored. The characteristics show how the presence and degree of the disease are depicted in the near-infrared fundus image. The image processor 230 analyzes the composed image, thereby determining whether it is applicable to the characteristics mentioned above. Thereby, information showing the name, presence, and degree of the lesion may be obtained.

Operation Example 3

The image processor 230 may determine the image quality of the composed image by analyzing the composed image obtained by removing the low-frequency components from the near-infrared fundus image. As the image quality thereof, there is the presence of a mixture of flares, etc. Generally, when a flare is mixed in the near-infrared fundus image, a very bright image region is present (other than the optic disc). The image processor 230 determines whether or not such an image region is present in the composed image in order to determine the presence of a mixed flare. It should be noted that because the image region corresponding to the optic disc is substantially circular or substantially oval, and because the blood vessels extend from this image region, it is possible, by considering these characteristics, to distinguish whether the very bright region corresponds to the optic disc or corresponds to the flare. The image processor 230 of this operation example functions as a "determining part."

Operation Example 4

In this operation example, the composed image is formed by the procedure of the embodiment mentioned above and three-dimensional scanning is conducted to form the three-dimensional image of the fundus Ef. The three-dimensional image may be a stack of data of multiple tomographic images or volume data based on this. The image processor 230 projects (accumulates) the three-dimensional image in the depth direction of the fundus Ef (z-direction) to form a projection image. The projection image is a two-dimensional image artificially expressing the surface shape of the fundus Ef. The image processor 230 performs image position adjusting process between the projection image and the composed image. The image position adjusting process is conducted by, for example, specifying the image region corresponding to the same distinctive site of the fundus Ef from both images and fitting the positions of the specified distinctive sites (the specified image regions).

Thereby, the position of the near-infrared fundus image and the position of the OCT image (three-dimensional image) may be matched via the projection image. Moreover, by adding image position adjusting process between the near-infrared fundus image and any fundus image, the position of any fundus image may be matched with the position of the OCT image via the projection image and the near-infrared fundus image. The image processor 230 of this operation example functions as an "image position adjusting part."

Any of the processes using the composed image in the embodiment mentioned above and the operation examples may be applied to the following Embodiment 2. Moreover, processes using the composed image are not limited to the above, and may be conducted by replacing the near-infrared fundus image used in any process with the composed image.

[Effects]

The effects of the fundus observation apparatus 1 will be described.

The fundus observation apparatus 1 comprises a configuration of photographing the fundus Ef using infrared light, a configuration of forming a tomographic image of the fundus Ef using the OCT, and a configuration of analyzing the photographed image (near-infrared fundus image) of the fundus Ef to remove the predetermined low-frequency components from the photographed image. The process of removing the low-frequency components includes the smoothing process, difference process, and composition process.

According to the fundus observation apparatus 1, the signal components may be effectively extracted from the near-infrared fundus image and contrast may be enhanced.

Moreover, in the difference process, the fundus observation apparatus 1 multiplies the near-infrared fundus image and/or the smoothed image by the prescribed weight before calculating the difference, allowing further enhancement of contrast to be attempted.

The fundus observation apparatus 1 removes the low-frequency components from each frame of the near-infrared moving image and successively forms composed images, thereby obtaining a near-infrared moving image with the low-frequency components removed. Furthermore, the fundus observation apparatus 1 executes the position adjustment between the subject eye E and the optical system for OCT measurement based on the near-infrared moving image with the low-frequency components removed. Thereby, the position adjustment may be conducted with higher precision and higher accuracy using the composed image with enhanced contrast. Moreover, at least one among alignment, focusing, and tracking are included in the position adjustment.

Moreover, according to the fundus observation apparatus 1, the scanning region of the signal light LS may be set based on the near-infrared moving image with the low-frequency components removed. Thereby, the scanning region may be set with a higher precision and higher accuracy using composed images with improved contrast.

Moreover, according to the fundus observation apparatus 1, the distinctive site of the fundus Ef may be specified based on the near-infrared moving image with the low-frequency components removed. Thereby, the specification of the image region corresponding to the optic disc, etc. and/or the specification of the image region corresponding to the lesion site may be conducted with a higher precision and higher accuracy using composed images with improved contrast.

Moreover, according to the fundus observation apparatus 1, image quality may be determined based on the near-infrared moving image with the low-frequency components removed. Thereby, image-quality determination may be conducted with a higher precision and higher accuracy using composed images with improved contrast.

Moreover, according to the fundus observation apparatus 1, the position of the near-infrared moving image with the low-frequency components removed and the position of the projection image of the three-dimensional image obtained at OCT measurement may be matched. Thereby, using composed images with improved contrast, the image position adjustment may be conducted with a higher precision and higher accuracy than before.

Figure 5A:
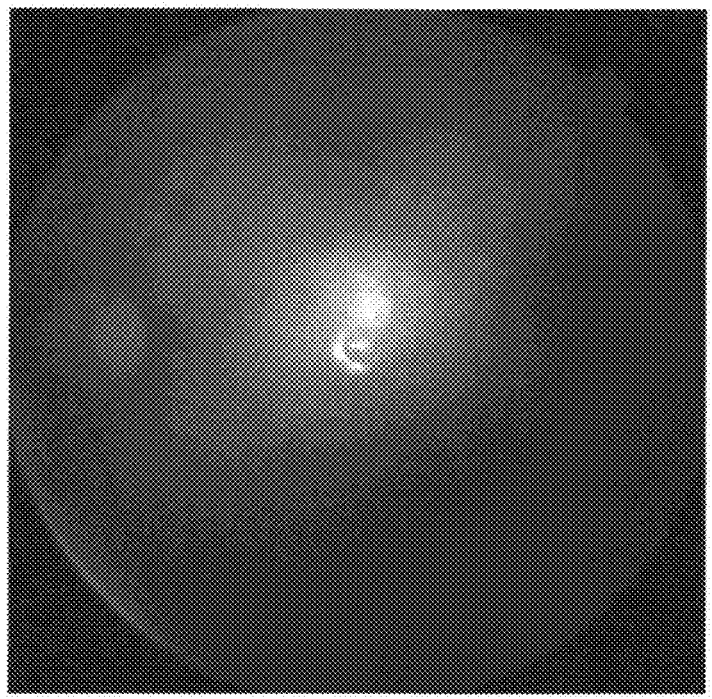
FIG. 5A is a diagram for explaining the effect of an embodiment of a fundus observation apparatus according to the present invention.
Figure 5B:
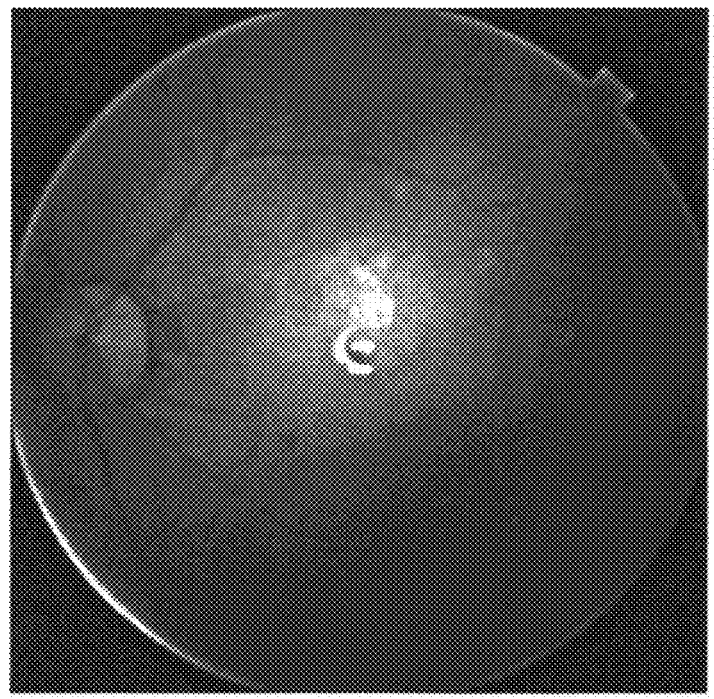
FIG. 5B is a diagram for explaining the effect of an embodiment of a fundus observation apparatus according to the present invention.

The effect when the low-frequency components are removed using this embodiment is explained with reference to FIG. 5A and FIG. 5B. FIG. 5A shows the original near-infrared fundus image. FIG. 5B shows the composed image that is obtained by conducting difference processing in which the smoothed image based on the near-infrared fundus image is multiplied by a weight w=0.8, and conducting composition processing in which the result of the difference processing is divided by 1−w=0.2 in order to adjust the luminance (contrast). As is evident from both images, the unclear fundus morphology in the near-infrared fundus image shown in FIG. 5A becomes clear in the composed image shown in FIG. 5B. Particularly, it may be understood that the image regions corresponding to the contour of the optic disc and the blood vessels are clear. Moreover, the white-spotted lesion site is also clear.

Embodiment 2

In this embodiment, the fundus observation apparatus configured such that the low-frequency components is removed from the near-infrared fundus image by a process different from the Embodiment 1 is explained.

[Configuration]

The fundus observation apparatus related to this embodiment comprises the same configuration as Embodiment 1 except for the image processor 230 (refer to FIG. 1 and FIG. 2). The configuration of the control system of this embodiment is shown in FIG. 6. Explanation of configurations other than the image processor 230 is omitted.

(Image Processor)

The image processor 230 of this embodiment comprises the Fourier transforming part 234, mask processing part 235, and inverse Fourier transforming part 236.

(Fourier Transforming Part)

The Fourier transforming part 234 forms an image in the frequency space (referred to as a spectral image) by conducting two-dimensional Fourier transformation on the near-infrared fundus image. The two-dimensional Fourier transformation may be any conversion process, for example, a discrete cosine transformation, in which frequency of the two-dimensional image may be obtained, in addition to the general two-dimensional Fourier transformation.

(Mask Processing Part)

The mask processing part 235 composes the mask image previously set in the frequency space mentioned above with the spectral image. The mask image is, for example, the band pass filter that removes at least the predetermined low-frequency components in the frequency space. More concretely, the mask image is a high pass filter that removes only the predetermined low-frequency components in the frequency space, or a band pass filter that removes both the predetermined low-frequency components and the predetermined high-frequency components.

The range of the removed frequency components is appropriately set based on the low-frequency components in real space which are the subject to be removed, the degree of enhancing the contrast, etc. The removal range of the frequency components may be a range set in advance or a range set by analyzing the spectral image.

(Inverse Fourier Transforming Part)

The inverse Fourier transforming part 236 forms the image with the low-frequency components removed from the original near-infrared fundus image in real space by conducting two-dimensional inverse Fourier transformation on the image formed by the mask processing part 235 (referred to as a mask composed image).

Based on the near-infrared fundus image with the low-frequency components removed in this manner, the fundus observation apparatus 1 may conduct various processes such as alignment, focusing, tracking, setting the scanning region (including follow-up), specifying distinctive sites and/or lesion sites, determining the name, presence and degree of the disease, determining the image quality, image position adjustment, etc.

[Effect]

The fundus observation apparatus related to this embodiment comprises a configuration of photographing the fundus Ef using infrared light, a configuration of forming a tomographic image of the fundus Ef using the OCT, and a configuration of analyzing the photographed image (near-infrared fundus image) of the fundus Ef to remove predetermined low-frequency components from the photographed image. The process of removing the low-frequency components includes Fourier transformation, mask processing, and inverse Fourier transformation.

According to the fundus observation apparatus 1, the signal components may be effectively extracted from the near-infrared fundus image and contrast may be enhanced.

Moreover, by conducting various processes such as alignment, focusing, tracking, setting the scanning region (including follow-up), specifying distinctive sites and/or lesion sites, determining the name, presence and/or degree of the disease, determining the image quality, image position adjusting process, etc. based on the near-infrared fundus image with the low-frequency components removed, the same effect as in the Embodiment 1 may be achieved.

Figure 7A:
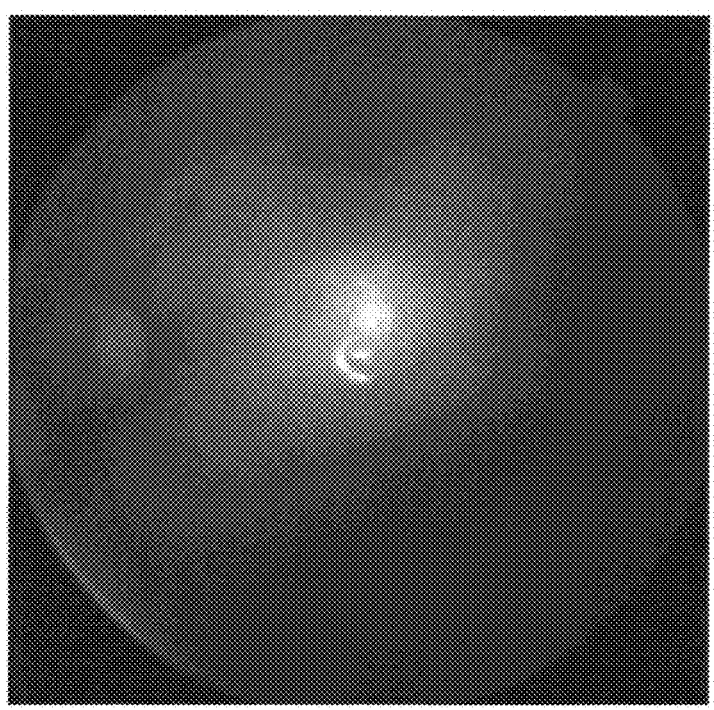
FIG. 7A is a diagram for explaining the effect of an embodiment of a fundus observation apparatus according to the present invention.
Figure 7B:
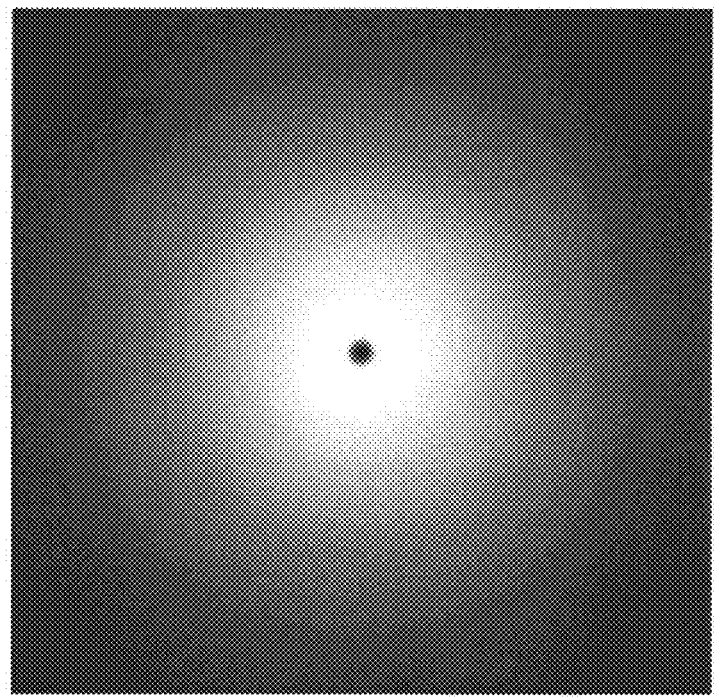
FIG. 7B is a diagram for explaining the effect of an embodiment of a fundus observation apparatus according to the present invention.
Figure 7C:
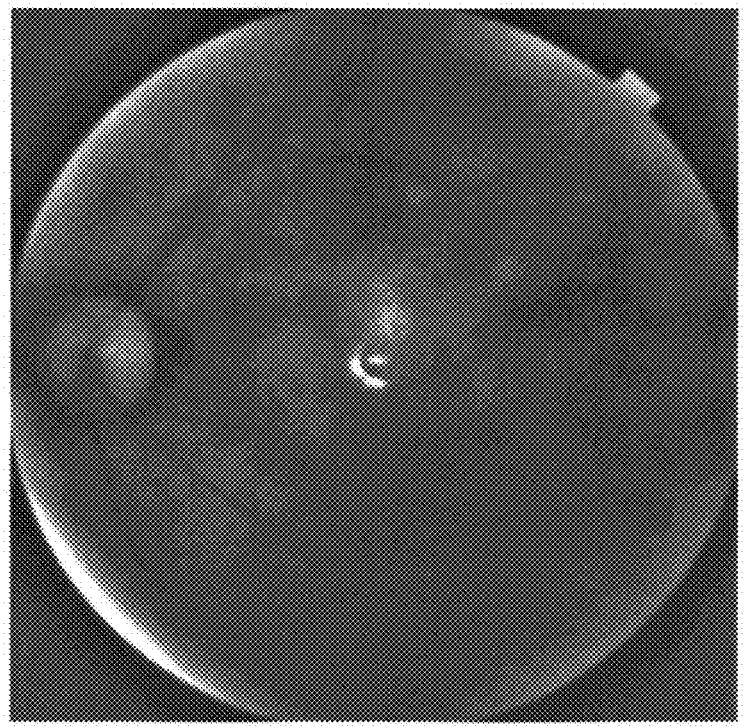
FIG. 7C is a diagram for explaining the effect of an embodiment of a fundus observation apparatus according to the present invention.

The effect when the low-frequency components are removed using this embodiment is explained with reference to FIGS. 7A to 7C. FIG. 7A shows the original near-infrared fundus image. FIG. 7B shows the adopted mask image. FIG. 7C shows the near-infrared fundus image with the low-frequency components removed using the mask image. As is evident from FIGS. 7A and 7C, the unclear morphology of the fundus in the near-infrared fundus image shown in FIG. 7A becomes clear in the near-infrared fundus image shown in FIG. 7C. Particularly, it is understood that the image regions corresponding to the contour of the optic disc and the blood vessels is clear. Moreover, the white-spotted lesion sites are also clear.

Modified Examples

The configuration described above is merely one example for favorably implementing the present invention. Therefore, it is possible to properly make arbitrary modification within the scope of the present invention.

In the embodiments mentioned above, the case of lighting the fundus with light in the near-infrared region has been particularly explained in detail; however, a configuration of lighting the fundus with light in the visible region (for example, green) may be adopted. This modified embodiment is used in, for example, a swept source type.

In the above embodiment, the position of the reference mirror 114 is changed to change the difference in optical path length between the optical path of the signal light LS and the optical path of the reference light LR, but the method of changing the difference in optical path length is not limited to this. For example, it is possible to change the difference in optical path length by moving the retinal camera unit 2 or the OCT unit 100 relative to the subject eye E and changing the optical path length of the signal light LS. Moreover, particularly if the object being measured is not a biological region, it is also effective to change the difference in optical path length by moving the object being measured in the depth direction (z-direction).

Computer programs for realizing the above embodiments can be stored in any kind of recording medium that can be read by a computer. As this recording medium, for example, an optical disk, a magneto-optic disk (CD-ROM, DVD-RAM, DVD-ROM, MO, and so on), and a magnetic storage (a hard disk, a floppy disk (TM), ZIP, and so on) can be used. Moreover, it is possible to store into a storing device such as a hard disk drive and a memory.

Besides, it is possible to transmit/receive this program through a network such as internet or LAN etc.

EXPLANATION OF THE SYMBOLS

1 Fundus observation apparatus
2 Retinal camera unit
10 Illumination optical system
30 Imaging optical system
43, 44 Galvano mirror
70 Scan driver
80 Focus driver
90 Optical system driver
100 OCT unit
130 Reference driver
200 Arithmetic and control unit
210 Controller
211 Main controller
212 Storage
220 Image forming part
230 Image processor
231 Smoothing part
232 Difference processing part
233 Composition processing part
234 Fourier transforming part
235 Mask processing part
236 Inverse Fourier transforming part
240A Display
240B Operation part
E Subject eye
Ef Fundus

What is claimed is:

1. A fundus observation apparatus, comprising:
a photographing part that photographs the fundus of a subject eye, a forming part comprising an optical system that irradiates signal light onto the fundus and interferes reflected light of the signal light from the fundus with reference light via a reference path and detects the resulting interference light, wherein the forming part forms a tomographic image of the fundus based on the detection result, and
an analyzing part that analyzes a photographed image of the fundus from the photographing part to delete predetermined low-frequency components from the photographed image, and wherein,
the analyzing part comprises:
a smoothing part that carries out a smoothing process on the photographed image to form a smoothed image,
a difference processing part that forms a difference image between the photographed image and the smoothed image by at least multiplying the photographed image and/or the smoothed image by a predetermined weight before forming the difference image, the difference image including at least a contour image of the optic disc in the fundus, a composition processing part that composes the photographed image from the photographing part and the difference image, thereby forming the photographed image with the low-frequency components removed, and the weight is set according to the degree of gradations in the photographed image of the fundus.

2. The fundus observation apparatus according to claim 1, wherein,
the weight is a value of 0.7 or more and 0.9 or less, and
the difference processing part makes the difference image of the smoothed image multiplied by this value and the photographed image.

3. The fundus observation apparatus according to claim 1, wherein,
the photographing part forms a moving image of the fundus by repeating the photographing at a specified time interval,
the analyzing part analyzes each frame of the moving image and removes the low-frequency components, and further comprising
a position adjusting part that adjusts the position of the subject eye and the position of the optical system based on the moving image with the low-frequency components removed.

4. The fundus observation apparatus according to claim 1, wherein,
the photographing part forms a moving image of the fundus by repeating the photographing at a specified time interval,
the analyzing part analyzes each frame of the moving image to remove the low-frequency components,
the optical system comprises a scanning part that scans the signal light with respect to the fundus, further comprising
a setting part that sets the scanning region of the signal light by the scanning part based on the moving image with the low-frequency components removed, and
the forming part forms a tomographic image based on the detection results of the interference light based on the signal light to the set scanning region.

5. The fundus observation apparatus according to claim 1, further comprising
a specifying part that analyzes the photographed image with the low-frequency components removed to specify a distinctive site in the photographed image.

6. The fundus observation apparatus according to claim 1, further comprising
a determining part that analyzes the photographed image with the low-frequency components removed to determine the image quality of the photographed image.

7. The fundus observation apparatus according to claim 1, wherein,
the optical system comprises a scanning part that two-dimensionally scans the signal light with respect to the fundus,
the forming part forms multiple tomographic images based on the detection results obtained by the two-dimensional scanning, forms a three-dimensional image based on the multiple tomographic images, and forms a projection image by projecting the three-dimensional image in the depth direction of the fundus, and further comprising
an image position adjusting part that adjusts the position of the projection image and the position of the photographed image with the low-frequency components removed.

* * * * *